(12) United States Patent
Choi

(10) Patent No.: US 12,196,649 B2
(45) Date of Patent: Jan. 14, 2025

(54) SAMPLE COLLECTOR FOR COLLECTION AND TRANSPORT OF BIOLOGICAL LIQUID SAMPLES AND MANUFACTURING METHOD THEREOF

(71) Applicants: SG Medical, Inc., Daegu (KR); Myung gyu Choi, Daegu (KR)

(72) Inventor: Myung gyu Choi, Daegu (KR)

(73) Assignees: Myung gyu Choi, Daegu (KR); SG Medical, Inc., Seoul (KR); IL SHIN FIBERCOATING CO., Yeongcheon-si (KR); Ho Young Kim, Daegu (KR)

( * ) Notice: Subject to any disclaimer, the term of this patent is extended or adjusted under 35 U.S.C. 154(b) by 904 days.

(21) Appl. No.: 17/331,601

(22) Filed: May 26, 2021

(65) Prior Publication Data

US 2022/0142620 A1    May 12, 2022

(30) Foreign Application Priority Data

Nov. 6, 2020   (KR) .................. 10-2020-0147694

(51) Int. Cl.
  *C12M 1/26*    (2006.01)
  *A61F 13/38*   (2006.01)
  *G01N 1/10*    (2006.01)

(52) U.S. Cl.
  CPC ............. *G01N 1/10* (2013.01); *A61F 13/38* (2013.01); *C12M 1/26* (2013.01)

(58) Field of Classification Search
  CPC ............ A61B 2010/0216; A61F 13/38; B01L 3/5029; C12M 1/26
  See application file for complete search history.

(56) References Cited

U.S. PATENT DOCUMENTS

| 4,718,889 A | * | 1/1988 | Blasius, Jr. | ............. A61F 13/38 604/1 |
| 5,899,622 A | * | 5/1999 | Gueret | ................. A45D 34/045 401/122 |
| 6,450,810 B1 | * | 9/2002 | Fischer | ............. B05C 17/00593 433/80 |

(Continued)

FOREIGN PATENT DOCUMENTS

| DE | 10 2020 116824 B3 | 7/2021 |
| JP | 2012-125195 A | 7/2012 |

(Continued)

*Primary Examiner* — Jonathan M Hurst
(74) *Attorney, Agent, or Firm* — Revolution IP, PLLC

(57) ABSTRACT

A manufacturing method of a sample collector for collection and transport of biological liquid samples, which includes a supporter, and a collecting part which is formed at an end portion of the supporter and to which fiber yarns are planted, includes the steps of: A) preparing two or more fiber yarns which are different from each other in at least one of length and width; and B) planting each of the fiber yarns to the collecting part based on a flocking method, wherein the step B) comprises the steps of: B1) mixing and putting the fiber yarns into a planting container so that the fiber yarns are distributed evenly; B2) inserting the collecting part into the planting container and applying adhesive onto the surface of the collecting part; and B3) planting the fiber yarns to the collecting part by electrostatic charge of each of the fiber yarns.

7 Claims, 3 Drawing Sheets

(56) References Cited

U.S. PATENT DOCUMENTS

| | | | |
|---|---|---|---|
| 2004/0018037 A1* | 1/2004 | Gueret | A46D 1/0238 |
| | | | 401/122 |
| 2004/0111105 A1* | 6/2004 | Schmieding | A61F 13/38 |
| | | | 606/162 |
| 2006/0142668 A1* | 6/2006 | Triva | C12M 33/02 |
| | | | 8/115.52 |
| 2010/0249649 A1* | 9/2010 | Larkin | A61B 10/02 |
| | | | 600/569 |
| 2011/0282243 A1* | 11/2011 | Nakatani | A45D 34/04 |
| | | | 606/162 |
| 2011/0306078 A1* | 12/2011 | Triva | G01N 1/10 |
| | | | 422/419 |
| 2016/0367227 A1* | 12/2016 | Triva | C12M 33/02 |
| 2021/0401408 A1* | 12/2021 | Holcombe | C12Q 1/689 |
| 2022/0160117 A1* | 5/2022 | Borsari | A46B 3/18 |
| 2022/0354244 A1* | 11/2022 | Cabon | A45D 34/042 |
| 2023/0270598 A1* | 8/2023 | Park | A61B 10/0045 |
| | | | 422/411 |
| 2023/0285204 A1* | 9/2023 | Kim | A61F 13/385 |

FOREIGN PATENT DOCUMENTS

| | | | |
|---|---|---|---|
| JP | 2014-083386 A | 5/2014 | |
| KR | 10-2011-0124626 A | 11/2011 | |
| WO | 2014-207598 A1 | 12/2014 | |
| WO | 2015-168808 A1 | 11/2015 | |
| WO | 2020/160555 A1 | 8/2020 | |

* cited by examiner

SAMPLE COLLECTOR FOR COLLECTION AND TRANSPORT OF BIOLOGICAL LIQUID SAMPLES AND MANUFACTURING METHOD THEREOF

BACKGROUND OF THE INVENTION

Field of the Invention

The present invention relates to a sample collector for collection and transport of biological liquid samples and a manufacturing method thereof, and more particularly, to a sample collector for collection and transport of biological liquid samples, which includes two or more fiber yarns which are different from each other in at least one of length and width and are disposed to a collecting part formed at one end portion of a supporter in order to easily collect biological liquid samples, and a manufacturing method of the sample collector.

Background Art

Recently, not only the flu breaking out by the flu virus every year but also new epidemics breaking out by SARS virus and corona virus have frequently broken out.

In order to check whether a person contracts the corresponding disease, collection of samples should be a priority, and various studies for effectively collecting samples have been made.

Conventionally, collection of samples using cotton swabs has been made in order to collect and transport biological liquid samples, such as bodily secretions containing viruses, and sample collectors with various forms and structures, except cotton swabs, have been developed.

Especially, cotton swabs can easily collect and transport biological liquid samples at very low costs. However, the cotton swabs can exactly collect liquid samples but lose lots of liquid samples since the liquid samples are absorbed into the cotton swabs, and in that there is a limit in grasping whether a person is infected with the disease since the cotton swabs collect a small quantity of samples.

As an example of a conventional art for manufacturing cotton swabs, Korean Patent Publication No. 10-2011-0124626 discloses a "cotton swab for cleaning and manufacturing method thereof".

The conventional art includes the steps of pressurizing non-woven fabric, fusing the pressurized non-woven fabric with ultrasonic waves to be attached to an end portion of a handle, forming a separation prevention groove to prevent separation of the non-woven fabric, and pressing and fixing the non-woven fabric.

The conventional art has an advantage in that the non-woven fabric can be fixed firmly, but has several disadvantages in that it needs additional process of forming a protrusion on the handle to which the non-woven fabric is attached, and in that it also requires a lot of process steps, such as pressing, fusing, and cutting using a high frequency fusion machine. Especially, the convention art is convenient to attach a material, such as cotton or non-woven fabric, with a certain area to the handle, but cannot use the corresponding process in order to fix materials, such as fiber yarns which do not absorb samples, to the end portion of the handle in order to collect samples.

In order to solve the problems, there have been various attempts to collect liquid samples using fiber yarns disposed on sample collectors, but it is difficult to attach fiber to the sample collector and it is not easy to collect liquid samples by the attached fiber.

SUMMARY OF THE INVENTION

Accordingly, the present invention has been made to solve the above-mentioned problems occurring in the prior arts, and it is an object of the present invention to provide a sample collector for collection and transport of biological liquid samples, which includes two or more fiber yarns which are different from each other in at least one of length and width and are attached to a collecting part formed at one end portion of a supporter by a simple process, thereby being manufactured easily and easily collecting biological liquid samples.

It is another object of the present invention to provide a manufacturing method of the sample collector to easily and accurately plant (attach) fiber yarns to the collecting part when each of the fiber yarns is planted to the collecting part.

To accomplish the above object, according to the present invention, there is provided a manufacturing method of a sample collector for collection and transport of biological liquid samples, which includes a supporter, and a collecting part which is formed at an end portion of the supporter and to which fiber yarns are planted, the manufacturing method including the steps of: A) preparing two or more fiber yarns which are different from each other in at least one of length and width; and B) planting each of the fiber yarns to the collecting part based on a flocking method, wherein the step B) includes the steps of: B1) mixing and putting the fiber yarns into a planting container so that the fiber yarns are distributed evenly; B2) inserting the collecting part into the planting container and applying adhesive onto the surface of the collecting part; and B3) planting the fiber yarns to the collecting part by electrostatic charge of each of the fiber yarns.

Furthermore, the manufacturing method further includes the step of: putting an adhesive remover, which contains any one among denatured alcohol and isopropyl alcohol, into the planting container in order to remove the adhesive applied to the collecting part.

Moreover, the fiber yarns include a plurality of short fiber yarns of the same length and a plurality of long fiber yarns of the same length.

Additionally, the short fiber yarns have a length selected from 0.4 mm to 0.8 mm, and the long fiber yarns have a length selected from 0.9 mm to 1.2 mm.

In addition, the fiber yarns include a plurality of narrow fiber yarns of the same width and a plurality of wide fiber yarns of the same width.

Moreover, the narrow fiber yarns have a width selected from 0.8 to 1.2 Dtex, and the wide fiber yarns have a width selected from 1.3 to 1.6 Dtex.

Furthermore, in the step A), each of the fiber yarns are made of a nonhydrophilic material or a material which does not absorb liquid.

Additionally, in the step A), each of the fiber yarns is made of any one or two or more mixed materials among polyamide, rayon, carbon fiber, and alginate.

In another aspect of the present invention, there is provided a sample collector manufactured by the manufacturing method described above, the sample collector includes: a supporter; a collecting part disposed at an end portion of the supporter; and two or more fiber yarns which are different from each other in at least one of length and width, the fiber yarns being planted to the collecting part and accepting collected liquid samples without absorbing the liquid samples.

The sample collector for collection and transport of biological liquid samples and the manufacturing method thereof according to the present invention can evenly plant fiber yarns since planting based on a flocking method.

Especially, the sample collector for collection and transport of biological liquid samples and the manufacturing method thereof according to the present invention can minimize the length and width of the fiber yarns, easily plant the fiber yarns, and easily accept liquid samples since planting both of two or more different fiber yarns which are different from each other in at least one of length and width.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Hereinafter, reference will be now made in detail to the preferred embodiments of the present invention with reference to the attached drawings. In the description of the present invention, when it is judged that detailed descriptions of known structures related with the present invention may make the technical idea of the present invention vague or obscure, the detailed descriptions of the known structures will be omitted.

FIGS. 1 to 4 are mimetic diagrams of a sample collector according to preferred embodiments of the present invention.

Figure 5:
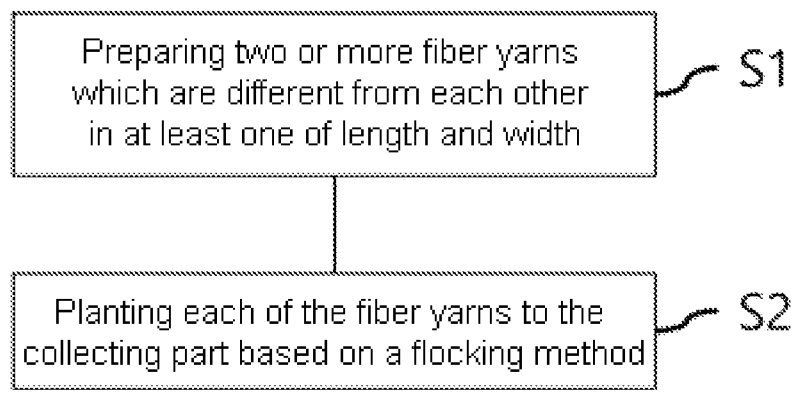
FIG. 5 is a flow chart of a manufacturing method of a sample collector according to a preferred embodiment of the present invention.
Figure 6:
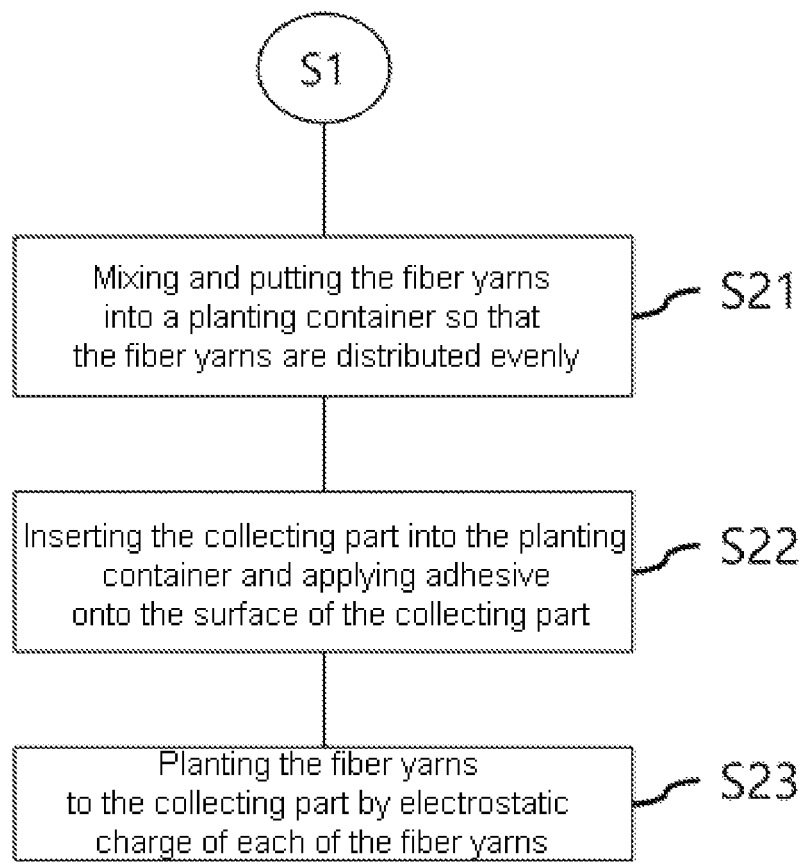
FIG. 6 is a flow chart of a manufacturing method of a sample collector according to another preferred embodiment of the present invention.

FIG. 5 is a flow chart of a manufacturing method of a sample collector according to a preferred embodiment of the present invention, and FIG. 6 is a flow chart of a manufacturing method of a sample collector according to another preferred embodiment of the present invention.

The manufacturing method of a sample collector according to the preferred embodiment is to collect and transport biological liquid samples.

The sample collector includes a supporter 10 and a collecting part 20. The collecting part 20 formed at one end portion of the supporter 10 includes a plurality of fiber yarns 30 planted.

The supporter 10 and the collecting part 20 may be made of any one among wood, synthetic resin material, fiber material and metallic material.

For example, the sample collector may include: a supporter made of a synthetic resin material; a collecting part 20 made of a synthetic resin material and disposed at one end portion of the supporter 10; and two or more fiber yarns 30 which are different from each other in at least one of length and width, the fiber yarns 30 being planted to the collecting part 20 and accepting collected liquid samples without absorbing the liquid samples.

The length of the fiber yarns 30 is selected from 0.4 mm to 3.2 mm, and the width of the fiber yarns 30 is selected from 0.4 Dtex to 3.5 Dtex.

'Dtex' is an index to show width, thickness, or others of fiber, for instance, the width of fiber is 1 tex when a yarn of 1,000 m is 1 g, the width of fiber is 1 Dtex when the yarn is 0.1 g. 'Dtex' may be varied according to the length and specific gravity of fiber yarns.

That is, it is general that the thickness (width) of fiber yarns is increased when the numerical value of Dtex is increased, but even though the numerical value of Dtex is equal, the smaller specific gravity of the fiber yarn is, the thicker the fiber yarn is.

The term, 'width', used in this specification indicates thickness of a strand of each fiber yarn, and the width has the meaning similar to thickness.

The sample collector according to an embodiment of the present invention may be manufactured by a manufacturing method of a sample collector. The manufacturing method of a sample collector includes the steps of: A) preparing two or more fiber yarns which are different from each other in at least one of length and width (Step S1); and B) planting each of the fiber yarns 30 to the collecting part 20 based on a flocking method (Step S2).

For instance, in the step S1, each of the fiber yarns 30 may be made of a nonhydrophilic material or a material which does not absorb liquid. In case that the fiber yarns are made of a nonhydrophilic material or a material which does not absorb liquid, it can prevent liquid samples collected by the fiber yarns 30 from being absorbed by the fiber yarns 30, minimize pollution caused by the liquid sample, and allow reuse of the sample collector through simple cleaning and disinfection.

For instance, in the step S1, each of the fiber yarns 30 may be made of any one or two or more mixed materials among polyamide, rayon, carbon fiber, and alginate.

Planting based on the flocking method is to plant a fiber layer made up of a plurality of the fiber yarns 30 to the surface of an object. When a plurality of the fiber yarns 30 are vertically planted onto the surface of the collecting part 20, it can minimize damage of the mucous membrane and facilitate collection of lots of liquid samples when liquid samples inside the human body is collected.

The flocking method is one among methods of planting the fiber yarns using static electricity or using a compressor or electrical or mechanical vibration after applying adhesive onto the surface of the collecting part 20.

For instance, the method using static electricity is a method of adding high-pressure static electricity of direct current, for example, 30,000V, after applying adhesive onto the surface of the collecting part 20 so that the fiber yarns 30 are strongly adhered onto the surface of the collecting part 20 by the static electricity. The fiber yarns 30 are vertically planted onto the surface of the collecting part 20 by static electricity, and the fiber yarns 30 are adhered on the surface of the collecting part 20 by the adhesive.

According to the flocking method using static electricity, the step S2 includes the steps of: B1) mixing and putting the fiber yarns 30 into a planting container so that the fiber yarns 30 are distributed evenly (S21); B2) inserting the collecting part 20 into the planting container and applying adhesive onto the surface of the collecting part 20 (S22); and B3) planting the fiber yarns 30 to the collecting part 20 by electrostatic charge of each of the fiber yarns 30.

Preferably, the adhesive used in the present invention is harmless, and may be natural adhesive, fiber adhesive (water-soluble adhesive-modified acryl polymer, water), or medical adhesive.

For instance, both end portions of each of the fiber yarns 30 are partially cut in order to increase a contact area with the collecting part 20, so have cut portions (not shown) or grooves (not shown).

In this instance, the collecting part 20 has protrusions (not shown) formed on the surface thereof so that the cut portions or the grooves of the fiber yarns 30 are put (adhered) onto the protrusions. At the time of charge, the cut portions or the grooves of the fiber yarns 30 can be adhered onto the protrusions more firmly.

In this embodiment, the end portion opposed to the end portion of the fiber yarn 30 combined with the collecting part 20, namely, the end portion exposed to the outside has a space for accepting liquid samples at the time of collection of samples.

The manufacturing method of the sample collector according to the preferred embodiment of the present invention may include a step of drying at temperature of 55° C. to 65° C., preferably, 60° C., after the step B3).

The manufacturing method of the sample collector according to the preferred embodiment of the present invention may further include a step of cleaning using inert gas, such as nitrogen, or air, for instance, compressed air, after the drying step. In the drying step and the cleaning step, each of the fiber yarns are firmly fixed onto the sample collector according to the preferred embodiment of the present invention, and the fiber yarns which are not adhered to the sample collector are removed from the sample collector.

The manufacturing method of the sample collector according to another preferred embodiment of the present invention may further include a step of putting an adhesive remover, which contains any one among denatured alcohol and isopropyl alcohol, into the planting container in order to remove the adhesive applied to the collecting part 20 after the step B3).

The adhesive remover is applied to the surface of the collecting part 20 and/or the fiber yarns 30 through ultrasonic vibration or a flow of the remover in order to remove the adhesive exposed to the outside, and is used to prevent the liquid samples from being polluted by the adhesive during collection of samples.

As another example, the adhesive may be applied not to the surface of the collecting part 20 but to the end portions of the fiber yarns 30, and it makes the fiber yarns 30 planted better with a small quantity of adhesive, compared with the case that the adhesive is applied to the entire surface of the collecting part 20. Moreover, it can prevent the liquid samples from being polluted by the adhesive even though the step of additionally supplying the adhesive remover to remove the adhesive existing at the portion where the fiber yarns 30 are not adhered to the surface of the collecting part 20 is omitted.

It would be understood that the fiber yarns 30 prepared in the step S1 are groups of two or more fiber yarns having predetermined length and width. For instance, the groups of the fiber yarns have the same width, but some group of the fiber yarns is relatively shorter and the other group is relatively longer, so that groups of fiber yarns having two different lengths may be planted.

The fiber yarns 30 may be three or more groups of fiber yarns, and the sample collector may be varied according to kinds and properties of sample objects to be collected.

Compared with the case that a plurality of fiber yarns having single width and length are planted, if fiber yarns having different lengths or widths are mixed and planted, it can reduce the overall length and width of the fiber yarns and facilitate planting.

For instance, the fiber yarns 30 may be a plurality of short fiber yarns of the same length and a plurality of long fiber yarns of the same length.

The short fiber yarns and the long fiber yarns are classified according to a difference in length, and the groups of fiber yarns which are relatively shorter are called short fiber yarns, and the groups of fiber yarns which are relatively longer are called long fiber yarns.

The fiber yarns include the short fiber yarns of the same length and the long fiber yarns of the same length, so that a difference in thickness of the fiber layer disposed on the collecting part 20 may be formed and it improves absorption of liquid samples by the fiber yarns since the liquid samples can be accepted more inwardly, compared with the case that there is no difference in thickness of the fiber layer.

It will be understood that the absorption of the liquid samples does not mean that the fiber yarns absorb the liquid samples but mean that the liquid samples are adsorbed between the fiber yarns by surface tension of the liquid samples.

Figure 1:
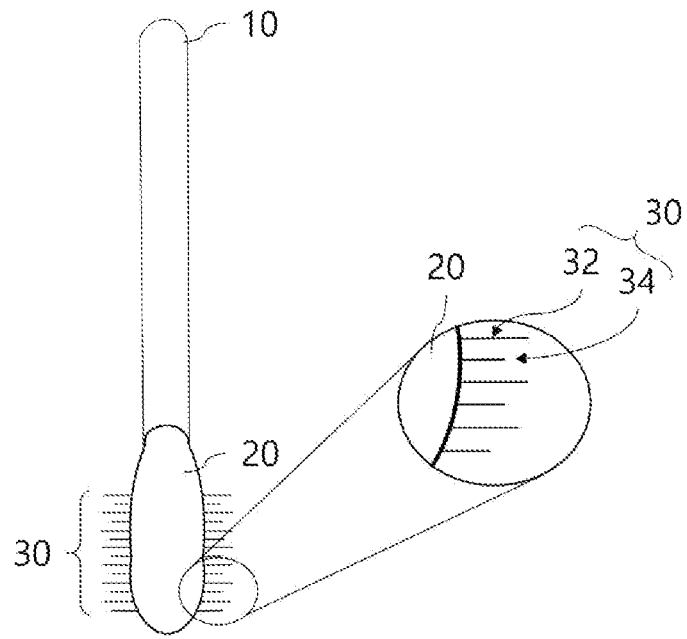
FIGS. 1 to 4 are mimetic diagrams of a sample collector according to preferred embodiments of the present invention.

For instance, as shown in FIG. 1, long fiber yarns 32 and short fiber yarns 34 which are narrow may be planted to the collecting part 20.

The short fiber yarns 34 may have a length selected from 0.4 mm to 0.8 mm, the long fiber yarns 32 may have a length selected from 0.9 mm to 1.2 mm, and the short fiber yarns 34 and the long fiber yarns 32 are 0.8 Dtex wide.

In another example, the fiber yarns may include a plurality of narrow fiber yarns of the same width and a plurality of wide fiber yarns of the same width.

The narrow fiber yarns and the wide fiber yarns are classified according to a difference in width, and the groups of fiber yarns which are relatively narrower are called narrow fiber yarns, and the groups of fiber yarns which are relatively wider are called wide fiber yarns.

The short fiber yarns, the long fiber yarns, the narrow fiber yarns, and the wide fiber yarns are classified according to relative concepts which may be applied to the same fiber yarns, and the fiber yarns may be short and narrow fiber yarns, short and wide fiber yarns, short and narrow fiber yarns, and long and wide fiber yarns.

The fiber yarns include the narrow fiber yarns of the same width (thickness) and the wide fiber yarns of the same width (thickness), so as to improve absorption of liquid samples by the fiber yarns.

As described above, it will be understood that the absorption of the liquid samples does not mean that the fiber yarns absorb the liquid samples but mean that the liquid samples are accepted between the fiber yarns.

Figure 2:
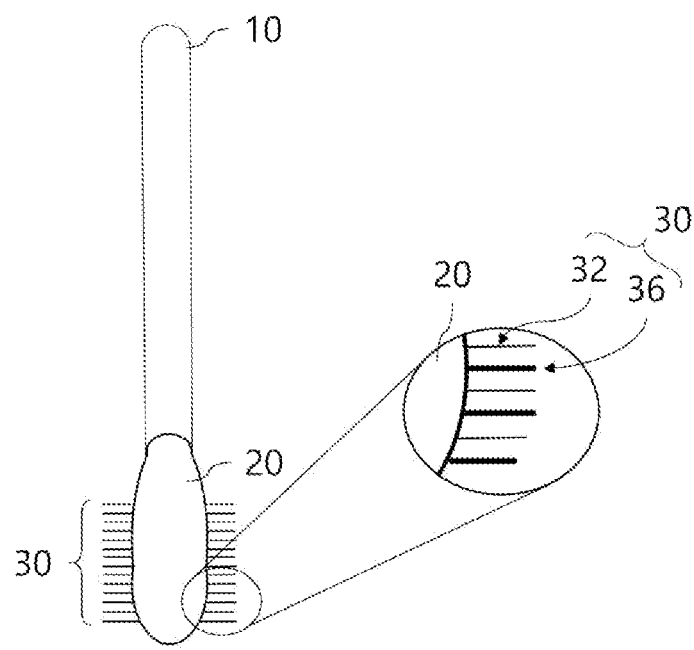

For instance, as shown in FIG. 2, the narrow fiber yarns 32 which are long and the wide fiber yarns 36 may be planted to the collecting part 20.

The narrow fiber yarns 32 may have a width selected from 0.8 to 1.2 Dtex, the wide fiber yarns 36 may have a width selected from 1.3 to 1.6 Dtex, and the narrow fiber yarns 32 and the wide fiber yarns 36 are 1.1 mm long.

Figure 3:
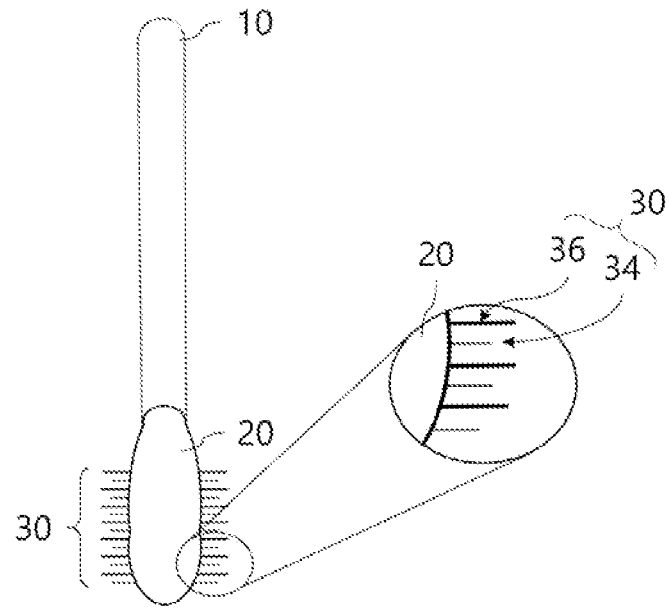

In a preferred embodiment, as shown in FIG. 3, the wide fiber yarns 36 which are long and the narrow fiber yarn 34 which are short may be planted to the collecting part 20.

For instance, the fiber yarns may be a plurality of the fiber yarns (wide fiber yarns which are long) which have the width of 1.5 Dtex and the length of 1.1 mm, and a plurality of the fiber yarns (narrow fiber yarns which are short) which have the width of 1.1 Dtex and the length of 0.8 mm. The combination of the fiber yarns makes the fiber yarns charged well and planted evenly since using fiber yarns which are thinner and shorter than the case that only a plurality of the fiber yarns with single length and single width, for instance, width of 2.0 to 3.0 Dtex and length of 1.2 mm) are planted. Especially, compared with the case that only the wide fiber yarns 36 which are long are planted, the combination of the fiber yarns according to the present invention can reduce the feeling of irritation when the sample collector is inserted into the nostril or the throat in order to collect liquid samples since collection of liquid samples is achieved by the combination of the short fiber yarns which are relatively thinner, namely, the narrow fiber yarns which are short, and the wide fiber yarns 36 which are long.

Moreover, because the fiber yarns are planted to the collecting part 20 to form a stepped part, the liquid samples can be evenly collected between the fiber yarns, and can be easily accepted and transported. That is, the relatively long fiber yarns first come into contact with the liquid sample, and the liquid samples move along the short fiber yarns through the long fiber yarns and are accepted to spaces among the fiber yarns. In this instance, if only the long fiber yarns are planted to the collecting part 20, it often occurs that the liquid samples are accepted only to the end portions of the fiber yarns and are not transported to the collecting part 20. However, according to the present invention, the liquid samples can be accepted to the entire spaces among the fiber yarns by the combination of the long fiber yarns and the short fiber yarns.

Figure 4:
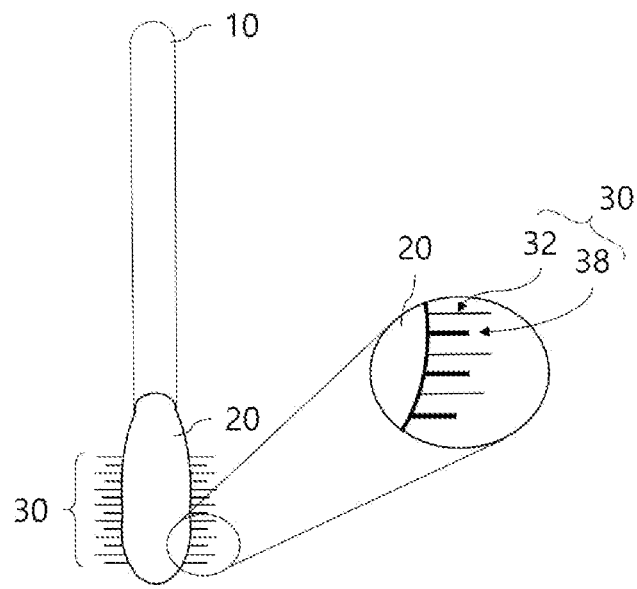

As a further example, as shown in FIG. 4, the wide fiber yarns 38 which are short and the narrow fiber yarns 32 which are long may be planted to the collecting part 20.

For instance,

For instance, the fiber yarns may be a plurality of the fiber yarns (wide fiber yarns which are short) which have the width of 1.5 Dtex and the length of 0.6 mm, and a plurality of the fiber yarns (narrow fiber yarns which are long) which have the width of 1.0 Dtex and the length of 1.1 mm. The combination of the fiber yarns makes the fiber yarns charged well and planted evenly since using fiber yarns which are thinner than the case that only a plurality of the fiber yarns with single length and single width, for instance, width of 3.0 Dtex and length of 0.9 mm) are planted.

Especially, the combination of the narrow fiber yarns 32 which are long and the wide fiber yarns 36 which are short according to the present invention can reduce the feeling of irritation since the narrow fiber yarns 32 which are long can collect the liquid samples while being pressed smoothly when the sample collector is inserted into the nostril or the throat in order to collect liquid samples, and can facilitate collection of samples since the wide fiber yarns 38 which are short prevent the narrow fiber yarns 32 which are long from being separated and support the narrow fiber yarns 32 which are long.

In this instance, as described above, because the fiber yarns are planted to the collecting part 20 to form a stepped part, the liquid samples can be evenly collected between the fiber yarns, and can be easily accepted and transported.

As a still further example, the fiber yarns may be made with porous nano-fiber. In this instance, since the fiber yarns are porous, the sample collector can collect and transport a great deal of liquid samples at the same time and reduce the size of the sample collector and the number of times being collected.

As described above, while the present invention has been particularly shown and described with reference to the example embodiments thereof, it will be understood by those of ordinary skill in the art that the embodiments are described as merely exemplary to make people understand easily. Therefore, it will be understood that various changes, modifications and equivalents may be made in the present invention without departing from the technical scope and idea of the present invention and belong to the protective scope of the present invention defined by the claims.

What is claimed is:

1. A manufacturing method of a sample collector for collection and transport of biological liquid samples, which includes a supporter, and a collecting part which is formed at an end portion of the supporter and to which fiber yarns are planted, the manufacturing method comprising the steps of:
   A) preparing two or more fiber yarns which are different from each other in at least one of length and width; and
   B) planting each of the fiber yarns to the collecting part based on a flocking method, wherein the step B) comprises the steps of:
   B1) mixing and putting the fiber yarns into a planting container so that the fiber yarns are distributed evenly;
   B2) inserting the collecting part into the planting container and applying adhesive onto the surface of the collecting part; and
   B3) planting the fiber yarns to the collecting part by electrostatic charge of each of the fiber yarns; wherein after the step B3), further comprising the step of: putting an adhesive remover, which contains any one among denatured alcohol and isopropyl alcohol, into the planting container in order to remove the adhesive applied to the collecting part.

2. The manufacturing method according to claim 1, wherein the fiber yarns include a plurality of short fiber yarns of the same length and a plurality of long fiber yarns of the same length.

3. The manufacturing method according to claim 2, wherein the short fiber yarns have a length selected from 0.4 mm to 0.8 mm, and the long fiber yarns have a length selected from 0.9 mm to 1.2 mm.

4. The manufacturing method according to claim 1, wherein the fiber yarns include a plurality of narrow fiber yarns of the same width and a plurality of wide fiber yarns of the same width.

5. The manufacturing method according to claim 4, wherein the narrow fiber yarns have a width selected from 0.8 to 1.2 Dtex, and the wide fiber yarns have a width selected from 1.3 to 1.6 Dtex.

6. The manufacturing method according to claim 1, wherein in the step A), each of the fiber yarns are made of a nonhydrophilic material or a material which does not absorb liquid.

7. The manufacturing method according to claim 1, wherein in the step A), each of the fiber yarns is made of any one or two or more mixed materials among polyamide, rayon, carbon fiber, and alginate.

* * * * *